(12) United States Patent
Fuhrman et al.

(10) Patent No.: US 8,374,801 B2
(45) Date of Patent: Feb. 12, 2013

(54) AUTOMATION OF INGREDIENT-SPECIFIC PARTICLE SIZING EMPLOYING RAMAN CHEMICAL IMAGING

(75) Inventors: Michael Fuhrman, Pittsburgh, PA (US); Ryan Priore, Wexford, PA (US); Oksana Olkhovyk, Pittsburgh, PA (US); Oksana Klueva, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 479 days.

(21) Appl. No.: 12/684,495

(22) Filed: Jan. 8, 2010

(65) Prior Publication Data

US 2010/0179770 A1 Jul. 15, 2010

Related U.S. Application Data

(60) Provisional application No. 61/143,562, filed on Jan. 9, 2009.

(51) Int. Cl.
*G01N 31/00* (2006.01)
(52) U.S. Cl. ........................................................ 702/28
(58) Field of Classification Search ...................... 702/28
See application file for complete search history.

(56) References Cited

U.S. PATENT DOCUMENTS

| | | | |
|---|---|---|---|
| 5,373,065 A | 12/1994 | Kitazawa et al. | |
| 5,377,003 A | 12/1994 | Lewis | |
| 5,504,332 A | 4/1996 | Richmond | |
| 5,546,475 A | 8/1996 | Bolle | |
| 5,567,628 A | 10/1996 | Tarcha et al. | |
| 5,841,577 A | 11/1998 | Wachman | |
| 5,870,189 A | 2/1999 | Uesugi et al. | |
| 5,880,830 A | 3/1999 | Schechter | |
| 6,058,322 A | 5/2000 | Nishikawa | |
| 6,081,612 A | 6/2000 | Gutkowicz-Krusin | |
| 6,091,843 A | 7/2000 | Horesh | |
| 6,316,772 B1 * | 11/2001 | Egelberg | 250/339.11 |
| 7,039,452 B2 | 5/2006 | McClane et al. | |
| 7,057,732 B2 | 6/2006 | Jorgenson et al. | |
| 7,120,173 B2 | 10/2006 | Roques et al. | |
| 7,379,179 B2 | 5/2008 | Nelson et al. | |
| 7,595,878 B2 * | 9/2009 | Nelson et al. | 356/335 |
| 2001/0006416 A1 | 7/2001 | Johnson | |
| 2006/0282223 A1 | 12/2006 | Lewis | |
| 2008/0032412 A1 * | 2/2008 | Lewis et al. | 436/164 |

OTHER PUBLICATIONS

Parker, J.R., Algorithms for Image Processing and Computer Vision, 1996, pp. 134-139.

Cal, et al., "A Novel Approach to Determining Particle Size Distributions of Pharmaceutical Powders by Near Infrared Spectroscopy", American Pharmaceutical review, vol. 8, No. 6 (Nov./Dec. 2005), pp. 51-56.

Vehring, et al., "The Characterization of Fine Particles Originating from an Unchanged Aerosol—Concentration Measurements on Droplet Chains", Journal of Aerosol Science, vol. 29, No. 9, Oct. 1998, pp. 1045-1061(17).

(Continued)

*Primary Examiner* — Aditya Bhat

(57) ABSTRACT

A system and method for determining at least one geometric property of a particle in a sample. A sample is irradiated to thereby generate Raman scattered photons. These photons are collected to generate a Raman chemical image. A first threshold is applied wherein the first threshold is such that all particles in the sample are detected. A particle in the sample is selected and a second threshold is applied so that at least one geometric property of the selected particle can be determined. At least one spectrum representative of the selected particle is analyzed to determine whether or not it is a particle of interest. The step of determining a second threshold may be iterative and automated via software so that candidate second thresholds are applied until a satisfactory result is achieved.

26 Claims, 14 Drawing Sheets

OTHER PUBLICATIONS

Hazel, Geoffrey G., "Object Level processing of Spectral Imagery for Detection of Targets and Changes Using Temporal Techniques", 2001 Proceedings of the SPIE, vol. 4381, p. 381-390.

Ghassermian, H. and Landgrebe, D.A., "Object-Oriented Feature Extraction Method for Image Data", Jun. 1998, IEEE Control Systems Magazine, pp. 42-48.

Aston, Edward A., "Multialgorithm Solution for Automated Multispectral Target Detection", 1999, Opt./ Eng. vol. 38, No, 4, p. 717-724.

Benz, U.C., Hofmann, P., Willhauck, G. Lingenfelder, I., Heynen, M., Multi-resolution, Object-oriented Fuzzy Analysis of Remote Sensing Data for GIS-Ready Information, ISPRS Journal of Photogrammetry & Remote Sensing, Jan. 2004, vol. 58, p. 239-258.

Treado, et al., "Near-infrared Acousto-Optic Filtered Spectroscopic Microscopy: A Solid-State Approach to Chemical Imaging", 1992, Applied Spectroscopy, vol. 46, No. 4.

Colarusso, et al., Infrared Spectroscopic Imaging: From Planetary to Cellular Systems, 1998, Applied Spectroscopy, vol. 52, p. 106A-120A.

Ortiz De Solorzano et al., Segmentation of Confocal Microscope Images of Cell Nuclei in Thick Tissue Sections, Mar. 1999, Journal of Microscopy, vol. 193, Pt. 3, pp. 212-226.

Adiga, et al., Efficient Cell Segmentation Tool for Confocal Microscopy Tissue Images and Quantitative Evaluation of FISH Signals, 1999, Microscopy Research and Technique, vol. 44, pp. 49-68.

* cited by examiner

Brightfield images of the droplets used for ISPS analysis (Batch 2 actuated sample)

Brightfield images of the droplets used for ISPS analysis (Batch 1 actuated sample)

Figure 13: Ingredient-Specific Particle Sizing of budesonide in representative Rhinocort Aqua® actuated droplets sampled from Batch 2: Brightfield reflectance/Raman fusion images after automated processing Figure 12: Ingredient-Specific Particle Sizing of budesonide in representative Rhinocort Aqua® actuated droplets sampled from Batch 1: Brightfield reflectance/Raman fusion images after automated processing

AUTOMATION OF INGREDIENT-SPECIFIC PARTICLE SIZING EMPLOYING RAMAN CHEMICAL IMAGING

RELATED APPLICATIONS

This application is entitled to priority pursuant to 35 U.S.C. §119(e) to U.S. Provisional Application No. 61/143,562, entitled "Automation of Ingredient-Specific Particle Sizing Employing Raman Chemical Imaging", filed on Jan. 9, 2009.

FIELD OF INVENTION

The invention relates generally to the use of Raman spectroscopic methods, including Raman chemical imaging and Raman spectroscopy for analyzing particles present in a sample. The invention relates more specifically to the use of these methods to determine at least one geometric property of particles present in a sample. Examples of geometric properties the present invention may be used to determine include, but are not limited to, particle size, morphology, and spatial distribution.

BACKGROUND

Surfaces form the interface between different physical and chemical entities, and the physical and chemical processes that occur at surfaces often control the bulk behavior of materials. For example, the rate of dissolution of drug particles in a biological fluid (e.g., stomach, intestinal, bronchial, or alveolar fluid in a human) can strongly influence the rate of uptake of the drug into an animal. Differences in particle size distribution between two otherwise identical compositions of the same drug can lead to significant differences in the pharmacological properties of the two compositions. Further by way of example, the surface area of a solid chemical catalyst can strongly influence the number and density of sites available for catalyzing a chemical reaction, greatly influencing the properties of the catalyst during the reaction. For these and other reasons, manufacturers often try to closely control particle size and shape. Associations between and among particles can also affect the pharmacological properties of substances in the particles, such as the ability of a substance to dissolve or become active in a biological system.

Numerous methods of analyzing particle sizes and distributions of particle sizes are known in the art, including at least optical and electron microscopy, laser diffraction, physical size exclusion, dynamic light scattering, polarized light scattering, mass spectrometric, sedimentation, focused beam backscattered light reflectance, impedance, radiofrequency migration, Doppler scattering, and other analytical techniques. Each of these techniques has a variety of limitations that preclude its use in certain situations. However, all of these techniques share a critical limitation that prevent effective use of the techniques for a wide variety of samples for which particle analysis would be valuable—namely, none of the prior art techniques is able to distinguish two particles that differ only in chemical composition. Put another way, a first particle having substantially the same size, shape, and weight as a second particle cannot be distinguished from the second particle in these methods. One method for using Raman spectroscopic methods for component particle analysis is described in U.S. Pat. No. 7,379,179 to Nelson et al., entitled "Raman Spectroscopic Methods for Component Particle Analysis", which is hereby incorporated by reference in its entirety.

In addition to distinguishing particles based on chemical composition, it is also useful to determine particle size and particle size distribution ("PSD"). Particle sizing of Active Pharmaceutical Ingredients ("API") and Excipients of Interest implemented using image analysis must be accurate because of the requirements of customers and the Food and Drug Administration ("FDA"). The FDA acknowledges a critical path opportunity for the development of methodologies for accurate and precise drug particle size measurements in suspension products, thereby minimizing the requirement for in vivo testing.

Batch comparison testing is an important part of product quality studies and is necessary in studying bioavailability ("BA") and/or establishing bioequivalence ("BE") for products including, but not limited to, nasal sprays. It is recommended by the FDA that in the BA and BE submission that PSD data is submitted for both new drugs ("NDAs") and abbreviated new drug applications ("ANDAs") for spray and aerosol formulations. Data must be presented prior to and post actuation since this information closely relates to the drug efficacy based on the dissolution rate of the particles. Such information can help establish the potential influence of the device on de-agglomeration.

Optical microscopy is currently the recommended method of assessing and reporting drug and aggregated drug PSD. However, such methodology is subjective and cannot be used with a high degree of confidence for formulated suspensions where drug particle sizing can be easily misjudged due to the presence of insoluble excipients.

Currently, no validated method exists for characterizing API particle size distribution in nasal aerosols and sprays dispite the request of such data for BE testing for NDAs and ANDAs. A qualitative and semi-quantitative estimation of drug and aggregated drug PSD is recommended based on optical microscopy, but insoluble suspending agents found in nasal spray formulations typically complicate the ingredient-specific particle size ("ISPS") determination. Therefore, there exists a need for an accurate and reliable system and method for performing such analysis on particle samples.

SUMMARY OF THE INVENTION

The present disclosure provides for a system and method for determining geometric properties of particles in a sample using Raman spectroscopic methods, including Raman chemical imaging and Raman spectroscopy. The invention disclosed herein overcomes the limitations of the prior art by implementing an individual particle based approach to particle analysis, thereby improving the dynamic range of particle analysis (increase the range of particles that can be detected). Such an approach is advantageous because it provides for more accurate detection and determination of the number of particles present in a sample and their sizes.

Raman chemical imaging is a versatile technique that is well suited to the analysis of complex heterogeneous materials. In a typical Raman chemical imaging experiment, a specimen is illuminated with monochromatic light, and the Raman scattered light is filtered by an imaging spectrometer which passes only a single wavelength range. The Raman scattered light may then be used to form an image of the specimen. A spectrum is generated corresponding to millions of spatial locations at the sample surface by tuning an imaging spectrometer over a range of wavelengths and collecting images intermittently. Changing the selected passband (wavelength) of the imaging spectrometer to another appropriate wavelength causes a different material to become visible.

The Raman chemical image is comprised of multiple images, each captured at a different wavelength. Contrast is generated in the images based on the relative amounts of Raman scatter or other optical phenomena, such as luminescence, that is generated by different species located throughout the sample. Since a spectrum is generated for each pixel location, chemometric analysis tools can be applied to the image data to extract pertinent information otherwise missed by ordinary univariate measures. The information contained within this multi-wavelength image cube is transformed into a single image plane for image analysis. Any method known in the art may be used to obtain the single plane image. In one embodiment, this may be achieved by extracting an image plane corresponding to a spectral peak of interest. Another method that may be used in another embodiment, which enhances signal-to-noise, is to sum the intensities of the spectral planes which are unique to particles of interest and from this subtract the average of background planes. Still another method that may be used, in another embodiment, is to perform a multivariate analysis to extract a small set of image(s) with high information content for further image processing. Examples of multivariate analysis include cluster analysis, principal component analysis (PCA), Cosine Correlation Analysis (CCA), Euclidian distance analysis (EDA), multivariate curve resolution (MCR), band t. entropy method (BTEM), Mahalanobis distance (MD), adaptive subspace detector (ASD), multivariate curve resolution (MCR), combinations thereof and others known in the art.

A spatial resolving power of approximately 250 nm may be useful for Raman chemical imaging using visible laser wavelengths. This is almost two orders of magnitude better than infrared imaging which is typically limited to 20 microns due to diffraction. In addition, image definition (based on the total number of imaging pixels) can be very high for Raman chemical imaging because of the use of high pixel density detectors (often one million plus detector elements).

The invention disclosed herein is advantageous over the prior art in several ways. For example, the systems and methods of the present disclosure improve the accuracy of particle size measurements by addressing at least three sources of error in particle size measurements including: (1) the non-uniform excitation illumination across the field of view of each image, (2) the dependency of Raman emission from individual particles on their size, morphology, and individual chemistry, and (3) that the physical process of image capture is subject to degradation by noise.

The prior art includes a method known as field flattening to compensate for non-uniform illumination. Prior art uses methods known as baseline correction and spectral normalization to implement field flattening. Other image analysis methods, include the use of an image of uniform field, morphological filters, frequency domain filters, and polynomial functions can be used to improve field flattening. Improvement of field flattening may allow a particle to be visible above background noise, and can be segmented and labeled as an object for further analysis.

The prior art sets a threshold level above background noise. This threshold is set so that the sizes of the particles detected in the Raman chemical image match the appearance of the sizes of the particles in the corresponding brightfield image. Particles with intensities above this threshold are detected as particles and particle sizes are determined from the detected pixels comprising the particles.

At least two problems are apparent from this process when the results are validated: (1) failure to detect all particles in a sample, and (2) failure to accurately size particles detected. Utilization of a global threshold alone may not be sufficient for accurate detection and size determination of particles. This is because particles with low Raman signals will not be detected and can be missed visually by a human performing validation. Particles may have low Raman signals either because they were situated in regions where the excitation illumination was low compared with the center of the field of view or because they were simply low emission particles.

Lowering the threshold intensity, in an attempt to detect more particles, may result in inaccurate sizing of particles. So, while some particles are correctly sized, the sizes of many particles may be too large or too small. This is because a global threshold will not be the optima threshold for every particle in a sample. This may also result in groups of smaller particles being identified as one larger particle. Reprocessing the image within the neighborhood of each detected particle to recompute the size may show that nearby particles were found to affect the automatically computed local threshold and affect the particle size.

The invention of the present disclosure addresses these issues by considering the particle detection step and the particle sizing step as two separate processes. This ensures more accurate particle sizing and is API specific. First, a low global threshold is set to guarantee the detection of all particles. Because of the noise in the Raman spectra, individual pixels which do not correspond to particles of interest may be inadvertently detected. The size of each detected particle is then determined using a threshold unique to each particle detected by applying the global threshold.

Since particle chemistry is just as important as particle size, the present disclosure also provides for a validation step wherein the chemical spectra of each particle is evaluated after the particle has been sized. This step is necessary because the first step of detecting potential particles is subject to noise and therefore the potential for interference exits. After each particle is sized its spectrum is evaluated. This may be achieved by verifying that a spectrum has been obtained, that the shape and appearance of the spectra is characteristic of a particle of interest, or comparing the spectrum to a reference spectrum of a particle type of interest to determine whether or not there is a match (i.e., API or excipient). Particles that do not share the spectrum of the particle of interest are rejected as not a particle of interest.

BRIEF DESCRIPTION OF THE DRAWINGS

FIG. 11B represents a Raman chemical image at 1657 $cm^{-1}$ of a single field of view of budesonide particles in a Rhinocort Aqua® droplet.

FIG. 11C represents normalized Raman spectra of the identified budesonide particles in a Rhinocort Aqua® droplet.

FIGS. 12 and 13 illustrate Brightfield reflectance/Raman fusion images for Batch 1 and Batch 2 samples, respectively.

DETAILED DESCRIPTION

The present disclosure provides for a system and method for analyzing particles in a sample. The method disclosed herein is useful for determining geometric properties of particles in a sample. The method also holds potential for evaluating other attributes of particles in a sample during particle analysis.

Figure 1:
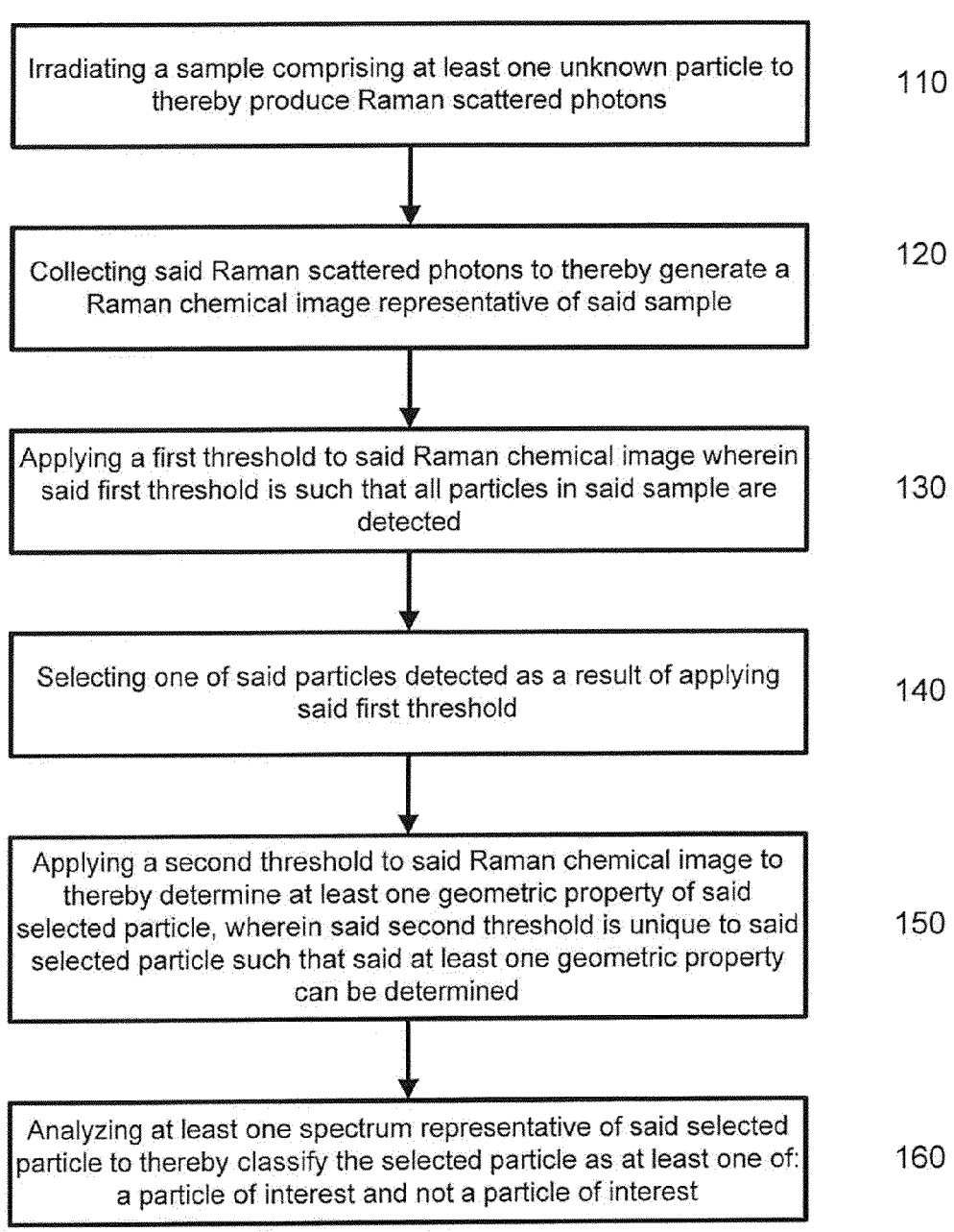
FIG. 1 is a flow chart diagram representing one embodiment of the present disclosure.

In one embodiment, illustrated by FIG. 1, the method 100 comprises irradiating a sample comprising at least one unknown particle to thereby produce Raman scattered photons in step 110. In step 120, said Raman scattered photons are collected to thereby generate a Raman chemical image representative of said sample. In step 130, a first threshold is applied to said Raman chemical image wherein said first threshold is such that all particles in said sample are detected. One particle of the particles detected as a result of applying the first threshold is selected in step 140. In step 150, a second threshold is applied to said Raman chemical image to thereby determine at least one geometric property of said selected particle, wherein said second threshold is unique to said selected particle such that said at least one geometric property can be determined. At least one spectrum representative of said selected particle is analyzed in step 160 to thereby classify the selected particle as at least one of: a particle of interest and not a particle of interest.

In one embodiment, the sample is irradiated using widefield illumination. In another embodiment, the sample is irradiated with substantially monochromatic light. In one embodiment, the determination of geometric properties of particles in the sample is achieved using a RCI hypercube. In such an embodiment, the intensity within the spectral peak is integrated at each pixel to create a working image with a higher signal-to-noise ratio than the peak intensity plane alone. In one embodiment, this can also be used as a method of base-line correction. The resulting working image depicts potential API particles as bright regions.

In one embodiment, the global threshold may be such that it is just above the background noise level. In such an embodiment, the background noise level is estimated and a global threshold barely above the background is implemented. In another embodiment, the global threshold may be some order of standard deviations of the noise above the average background intensity. In another embodiment, the global threshold may comprise three standard deviations of the noise above the average background intensity. Although a global threshold may ensure that all particles in a sample are detected (although with inaccurate sizes), there is also the possibility that some noise will be detected. The second threshold and validation steps account for this.

In one embodiment, the second threshold is determined by: individually processing the edges and brightness of each detected particle. The edges may be detected by computing the gradient of the working image to find the pixels where the intensity changes most rapidly. The pixels corresponding to the steepest edges can be identified and the average intensity of the edge pixels computed. This average intensity can then be used as the second threshold. In one embodiment, these steps can be performed for each particle detected in the sample. In another embodiment, the second threshold comprises a fraction of the peak intensity of the selected particle above the background intensity. In another embodiment, this fraction may comprise one half. Whatever method is used to determine the second threshold, it will be a threshold unique to the selected particle so that at least one geometric property can be accurately determined.

In one embodiment, the invention disclosed herein may be automated. This may be achieved via software. In one embodiment, the determination of a second threshold method may be iterative, meaning that the software will continue to apply one or more different particle specific thresholds ("candidate second thresholds") to a selected particle until a satisfactory result is achieved. A result is satisfactory when the results can be trusted. In one embodiment, this is measured using Rose's Criterion wherein object intensity is five standard deviations above the average background. The software then repeats this method, detecting and measuring the size of each particle until all of the individual particles present in the sample are detected and measured. This adaptive embodiment may provide for a feedback loop in which information received from the application of a second threshold is evaluated to determine whether or not is it satisfactory. If the result is satisfactory, then this threshold may be applied to assess the particle. If the result is not satisfactory, then a different second threshold is applied and evaluated to determine if a satisfactory result is reached. This feedback loop can continue until the satisfactory result is reached.

In one embodiment, the method may be adaptive in that the processing takes place in each local region while continuously adjusting threshold levels until a satisfactory result is achieved. Such adaptive processing may be useful for the situation where a region thought to contain one particle is found to actually contain one or more particle. The adaptive processing may iteratively continue such that if more than one particle is detected a unique and improved threshold is determined for each subsequently detected particle.

It is further contemplated by the present disclosure that the system and method disclosed herein may hold the potential for parallel processing. In such an embodiment, one or more systems may be configured in such a way that allows for more than one particle to be processed simultaneously. This may be achieved through a computer network or other configuration.

Said second threshold is such that at least one geometric property of the selected particle can be determined. This geometric property can be any property that may be of interest in particle analysis. In one embodiment, the geometric property is characteristic of the size of the particle. In another embodiment, the geometric property is characteristic of the particle size distribution. In yet another embodiment, the geometric property can be selected from the group consisting of: an area, a perimeter, a feret diameter, a maximum chord length, a shape factor, an aspect ratio of the particle, other geometric properties known in the art and combinations thereof.

At least one spectrum of said selected particle is analyzed in the validation step. This validation can be achieved in several ways. Implementing this validation step holds potential for reducing the number of false positives (i.e., the number of particles thought to be a particle of interest that are not actually a particle of interest), making assessment of the sample more accurate. In one embodiment, said validation may comprise confirming that a spectrum is in fact obtained from the selected particle. In another embodiment, said validation may comprise confirming the attributes of the spectrum obtained from the selected particle. This may mean that the spectrum looks like one would expect a spectrum is characteristic of the particle of interest (i.e., does it have a proper shape). In yet another embodiment, the validation step may comprise comparing at least one spectrum obtained from the selected particle to at least one reference spectrum. This reference spectrum may comprise the particle of interest or an excipient or other substance in the sample. This reference spectrum may be one of many reference spectra in a reference database which can be searched depending on the particular particle of interest, excipient, or other substance. The database may comprise more than one reference spectra of one particular particle. It may also comprise two or more reference spectra corresponding to two or more different particles of interest, excipient, or other substance.

Figure 2:
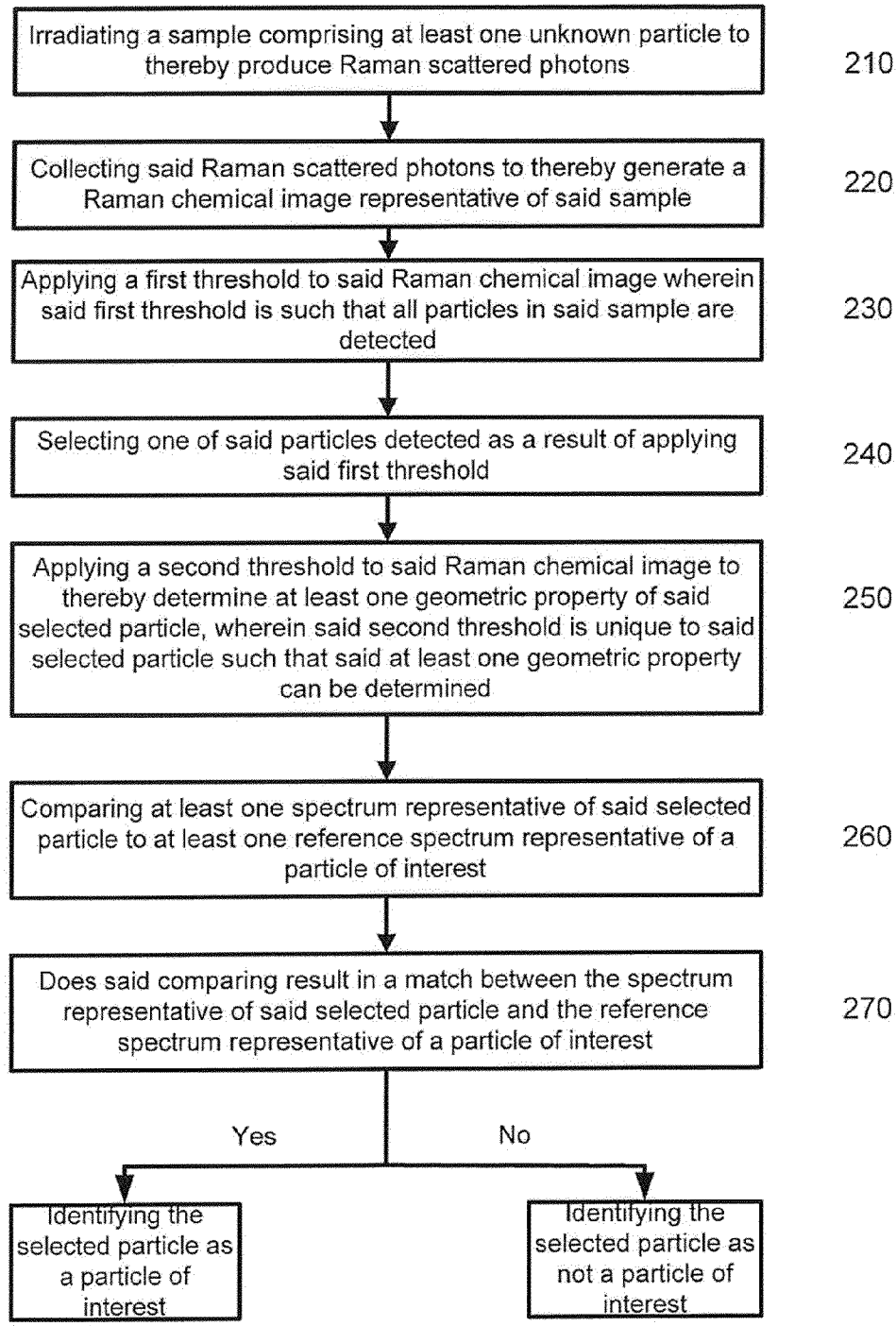
FIG. 2 is a flow chart diagram representing one embodiment of the present disclosure.

FIG. 2 illustrates one embodiment of the present disclosure in which a reference spectrum is used in the validation step. The method 200 comprises illuminating a sample comprising at least one unknown particle to thereby produce Raman scattered photons in step 210. These photons are collected in step 220 to thereby generate a Raman chemical image representative of said sample. In step 230, a first threshold is applied to said Raman chemical image wherein said first threshold is such that all particles in said sample are detected. One of said particles detected as a result of applying said first threshold is selected in step 240. In step 250 a second threshold is applied to said Raman chemical image to thereby determine at least one geometric property of said selected particle, wherein said second threshold is unique to said selected particle such that that said at least one geometric property can be determined. In step 260, at least one spectrum representative of said selected particle is compared to a reference spectrum representative of a particle of interest. This comparison is performed to determine whether or not there is a match between the spectrum representative of the selected particle and the reference spectrum representative of the particle of interest 270. If there is a match, the selected particle is identified as a particle of interest 280. If there is not a match, the selected particle is rejected as not a particle of interest 290.

Figure 3:
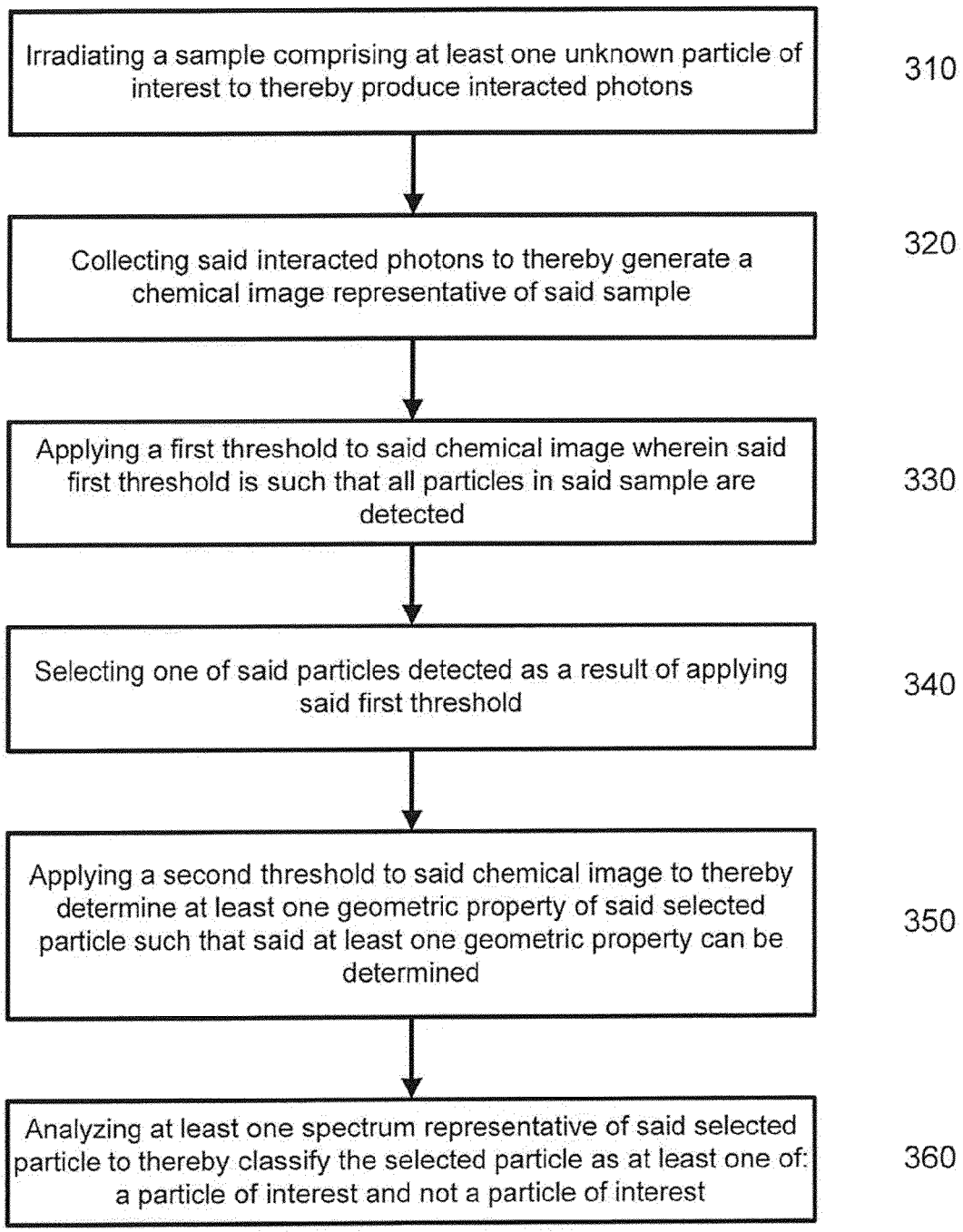
FIG. 3 is a flow chart diagram representing one embodiment of the present disclosure.

In another embodiment, illustrated by FIG. 3, the method 300 comprises irradiating a sample comprising at least one unknown particle of interest to thereby produce interacted photons in step 310. In one embodiment, these interacted photons are selected from the group consisting of: photons scattered by said sample, photons reflected by said sample, photons absorbed by said sample, photons emitted by said sample, and combinations thereof. In step 320, the photons are collected to thereby generate a chemical image representative of the sample. In step 330, a first threshold is applied to the spectroscopic image wherein said first threshold is such that all particles in said sample are detected. One of said particles detected as a result of the first threshold is selected in step 340. A second threshold is applied in step 350 to thereby determine at least one geometric property of the selected particle wherein the second threshold is unique to said second threshold such that a geometric property can be determined. In step 360 at least one spectrum representative of the selected particle is analyzed to thereby classify the selected particle as at least one of: a particle of interest or not a particle of interest.

In one embodiment, the method may further comprise repeating the steps enumerated herein for one other unknown particle present in said sample. The steps may also be repeated for each unknown particle detected in said sample.

In another embodiment, the method disclosed herein may further comprise fusing a Raman chemical image of a sample with a bright field image of said sample to thereby generate a fused image. This fused image can then be analyzed to determine at least one geometric property of at least one unknown particle in a sample.

Figure 4:
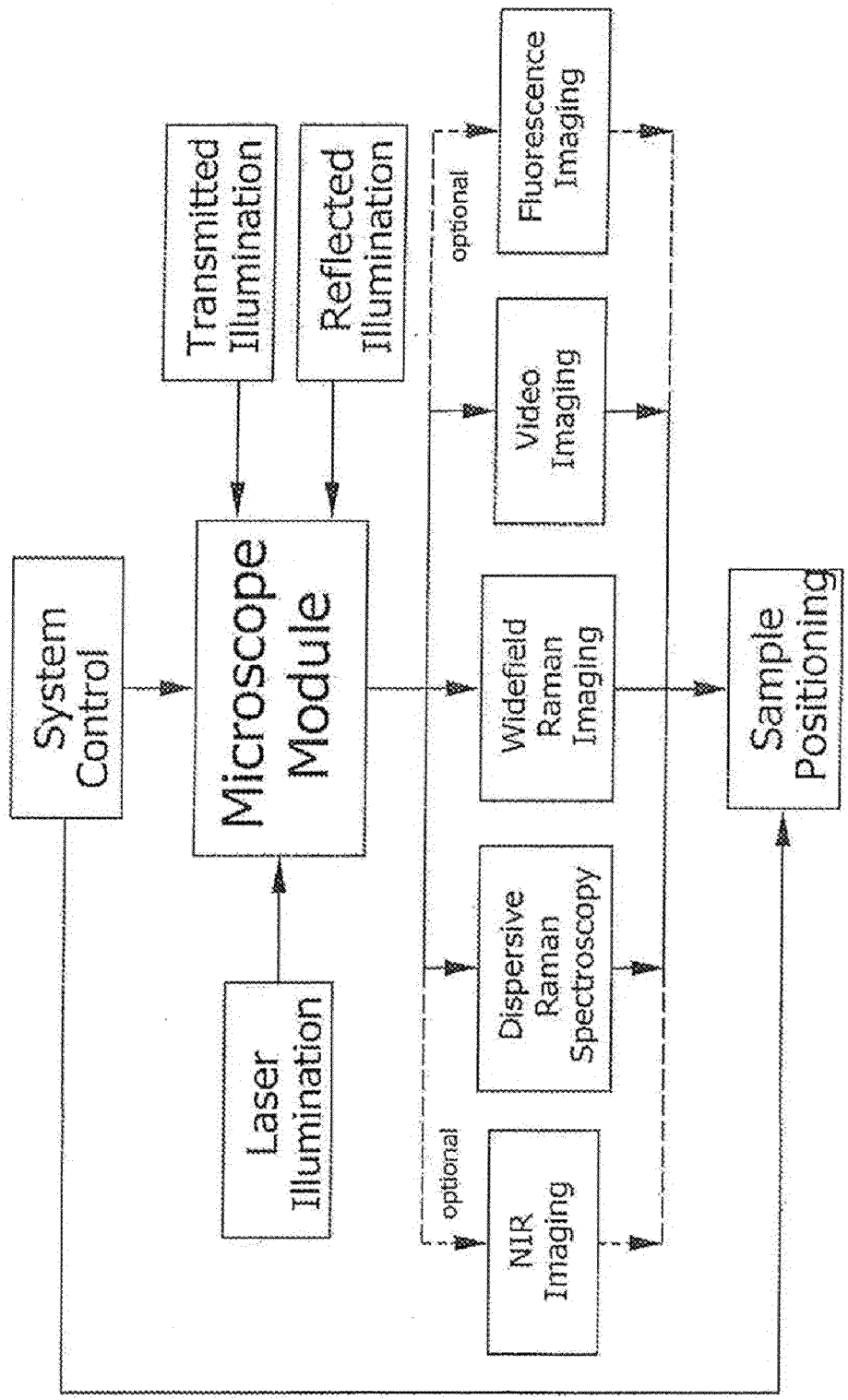
FIG. 4 is a schematic of an exemplary system that may be used to achieve the methods of the present disclosure.

FIG. 4 is a schematic representation of one system that may be used to perform the method of the present disclosure.

Figure 5A:
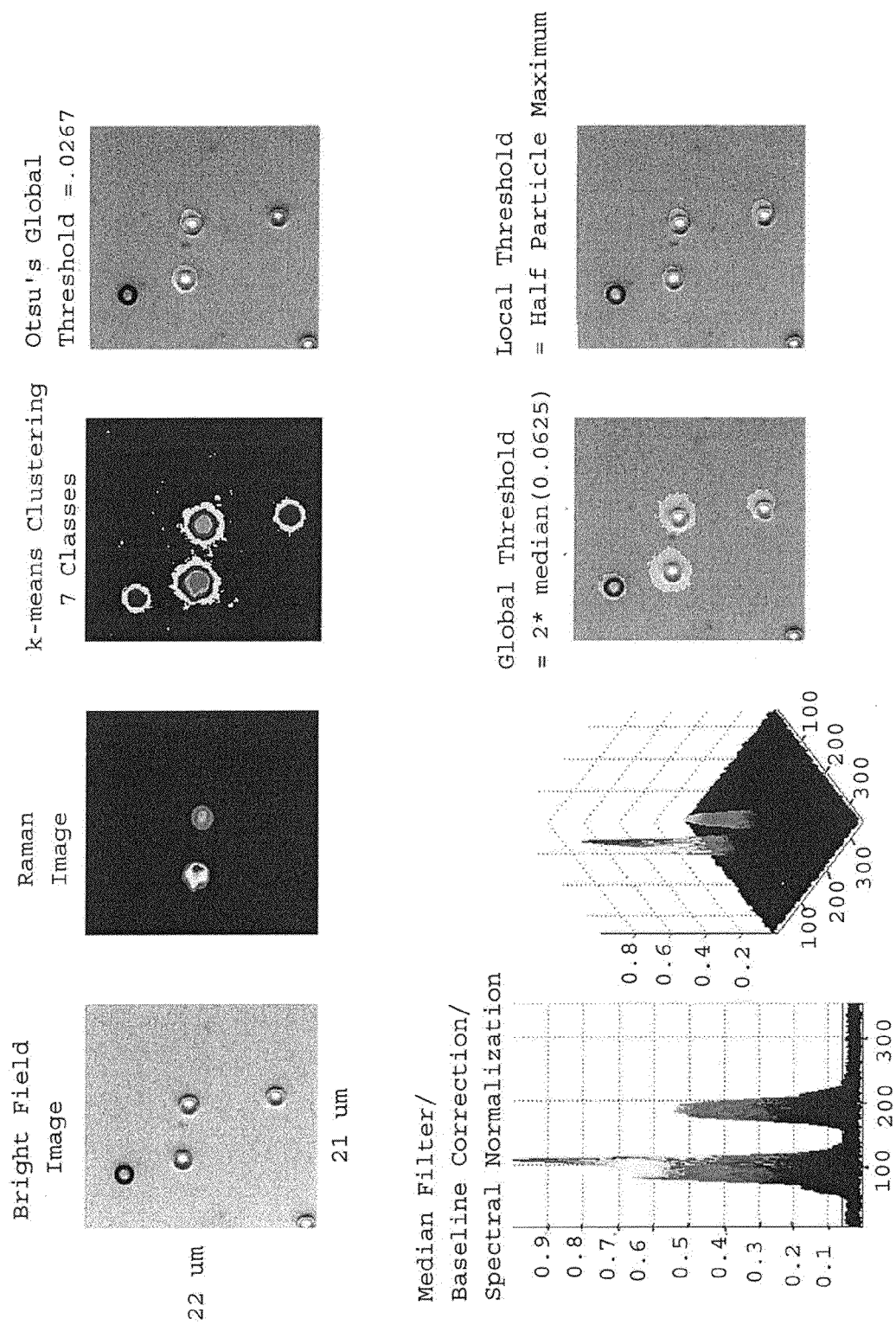
FIGS. 5A and 5B illustrate further explanation of the methods of the present disclosure.
Figure 5B:
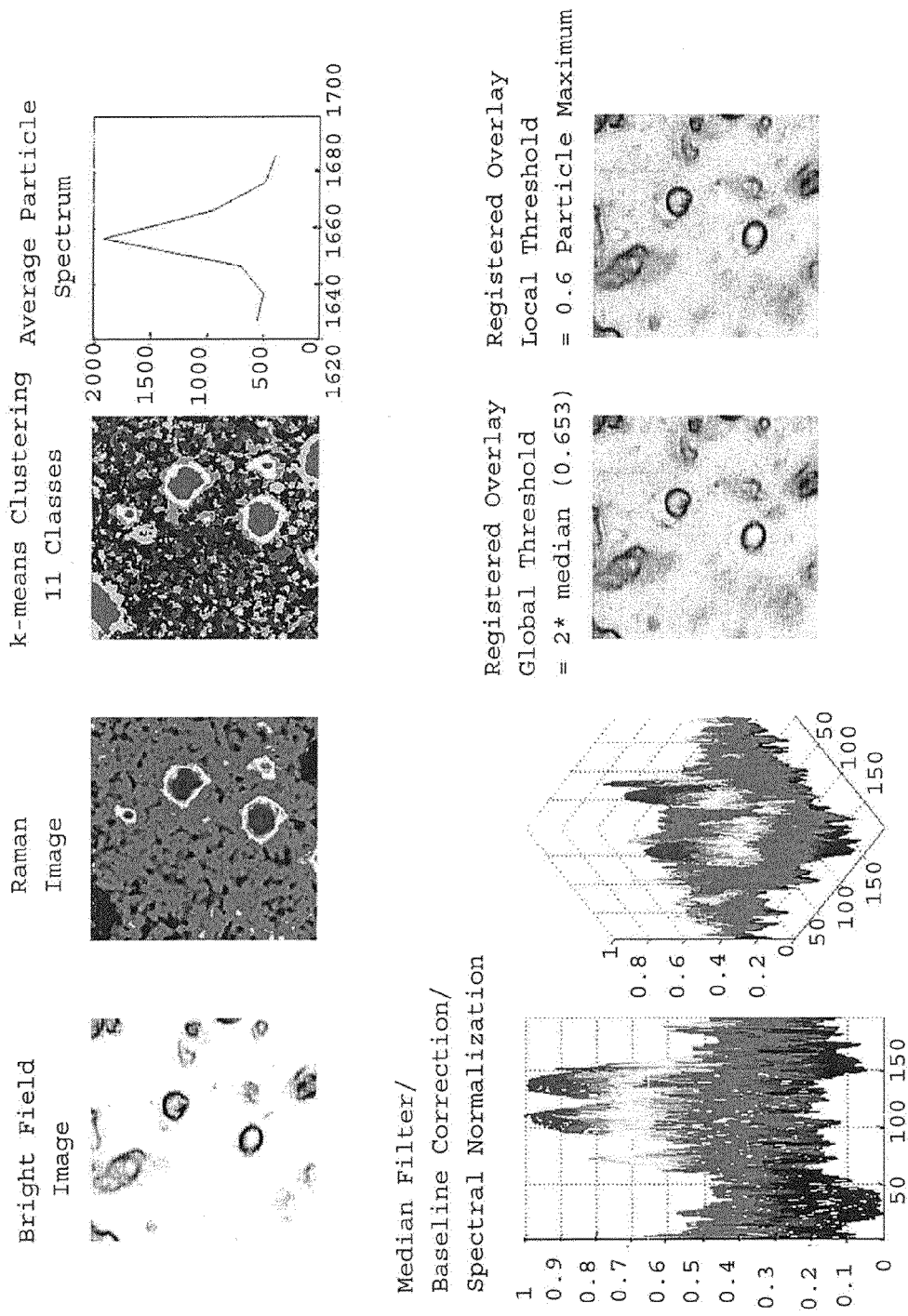
Figures 6A, 6B, 6C:
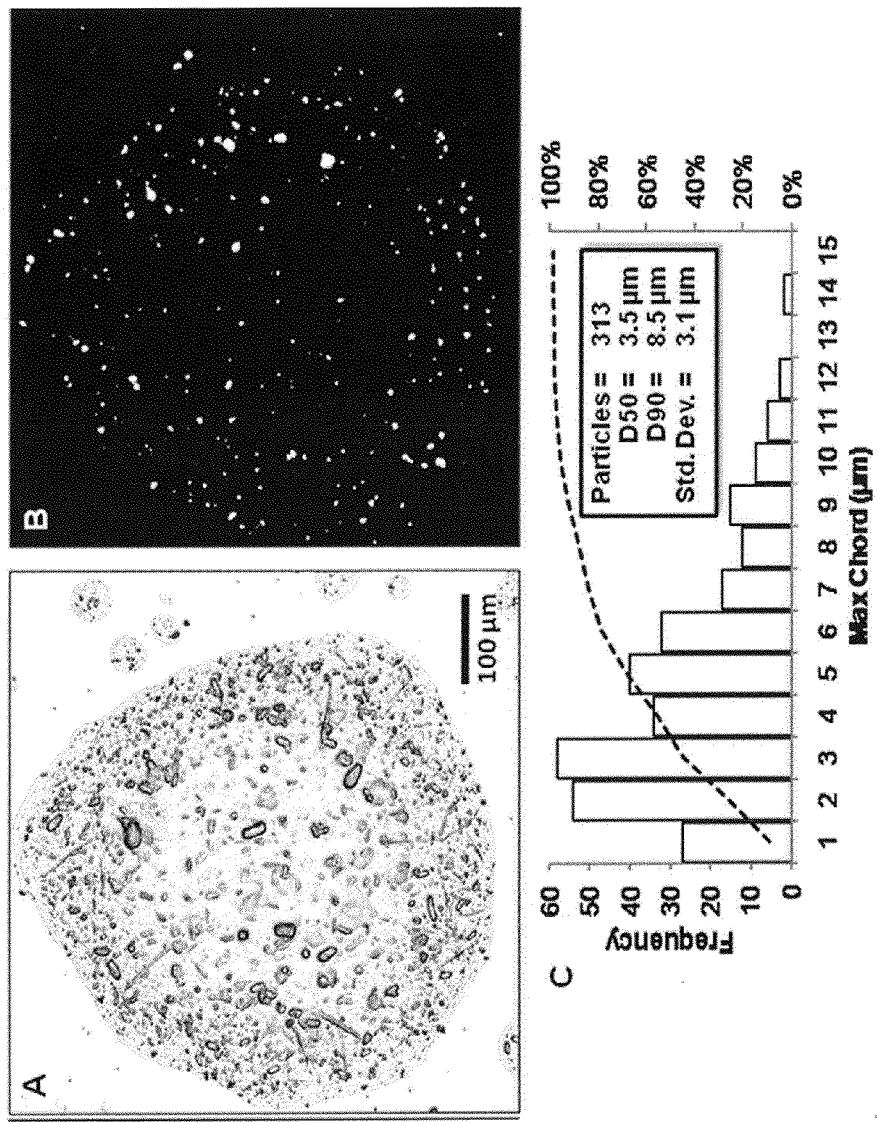
FIG. 6A represents a brightfield reflectance optical image of a Rhinocort Aqua® droplet.
FIG. 6B represents a Raman image of budesonide particles after global processing corresponding to FIG. 6A.
FIG. 6C illustrates the PSD of the Rhinocort Aqua API, budesonide.

FIGS. 5A and 5B are provided to further illustrate the advantages of the present invention, implementing a particle-specific analysis method. FIGS. 6A-6C illustrate global processing of brightfield and Raman chemical images of a Rhinocort Aqua® droplet, yielding a total of 313 particles with a maximum chord of 3.5±3.1 µm. Due to secondary scattering and the reliance upon spectral normalization to flat-field the chemical image, medium to large particles are typically oversized while small particles are sometimes lost. FIG. 6A represents a brightfield reflectance optical image of a Rhinocort Aqua® droplet, FIG. 6B corresponds to a Raman image of the budesonide particles after global processing, and FIG. 6C represents the PSD of the a Rhinocort Aqua® API, budesonide.

Figures 7A, 7B, 7C:
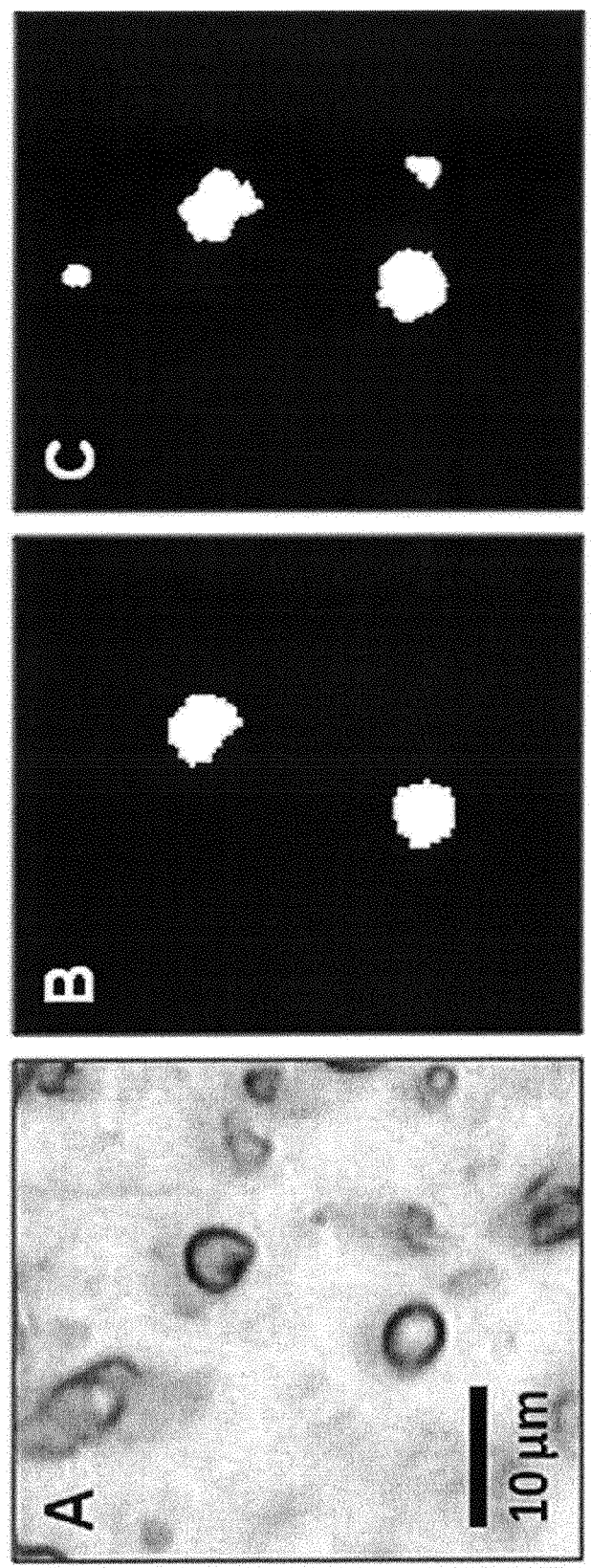
FIG. 7A represents a single field of view of budesonide particles in a Rhinocort Aqua® droplet.
FIG. 7B represents a global processed Raman chemical image.
FIG. 7C represents a local processed Raman chemical image.
Figure 7D:
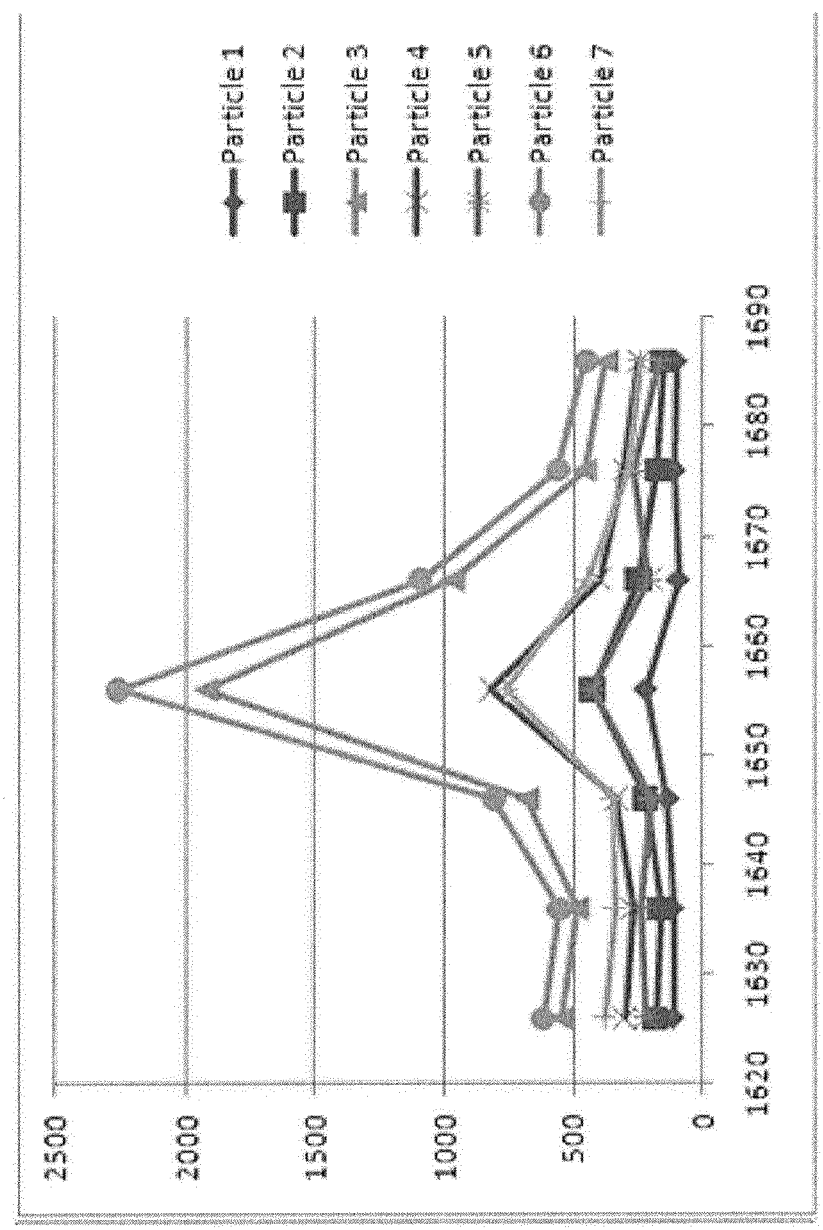
FIG. 7D illustrates the representative Raman spectra of particles in the sample.

FIGS. 7A-7D illustrate a comparison of global and local processing of a Rhinocort Aqua® droplet. FIG. 7A represents a brightfield reflectance optical image, FIG. 7B represents a global processed Raman chemical image, FIG. 7C represents a local processed Raman chemical image, and FIG. 7D represents the Raman spectra of the locally processed particles.

It is further contemplated by the present disclosure that the system and method provided for herein may implement other spectroscopic and/or imaging modalities including but not limited to: fluorescence, infrared (including short wave infrared, near infrared, mid infrared, and far infrared), ultraviolet, visible, others known in the art, and combinations thereof.

It is also contemplated by the present disclosure that the system and method disclosed may be applied to other fields including but not limited to threat detection, anatomic pathology, and forensics.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the embodiments of the disclosure, it is noted that other variations and modification will be apparent to those skilled in the art, and may be made without departing from the spirit of the disclosure.

EXAMPLES

Two different batches of nasal spray suspension (Rhinocort Aqua®) containing an insoluble corticosteroid AP (budesonide) and multiple excipients were analyzed to characterize the budesonide particle size distribution in the samples. Approximately 1000 particles of the API were counted for each batch using wide-field RCI (Falcon II™ ChemImage, Corporation, Pittsburgh, Pa.). The chemical identity of the budesonide particles was confirmed for each pixel against a Raman spectral library. Particle size information was obtained for each identified particle using an automated image processing and analysis algorithm. The ISPS determined from the RCI was compared to a complementary brightfield optical image. Statistical analysis of the total drug PSD for each batch based on a Kol-Smirnov goodness-of-fit hypothesis test was calculated to compare to the batches.

Figure 9:
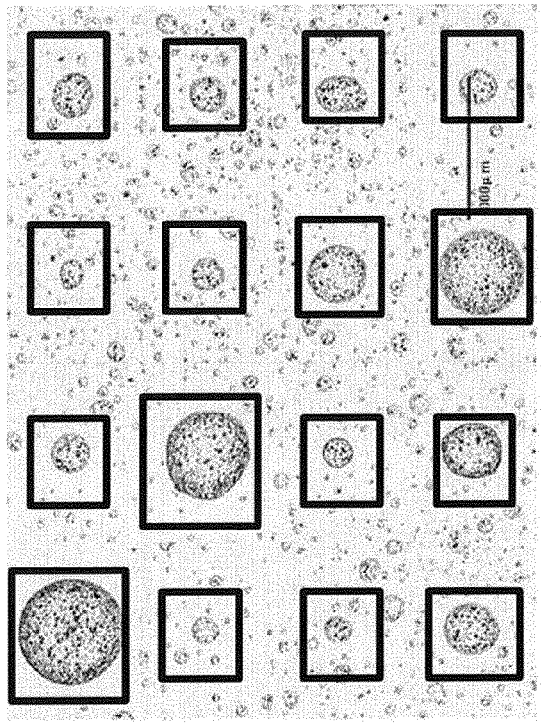
FIGS. 8 and 9 illustrate brightfield images of Batch 1 and Batch 2 samples, respectively.
Figure 8:
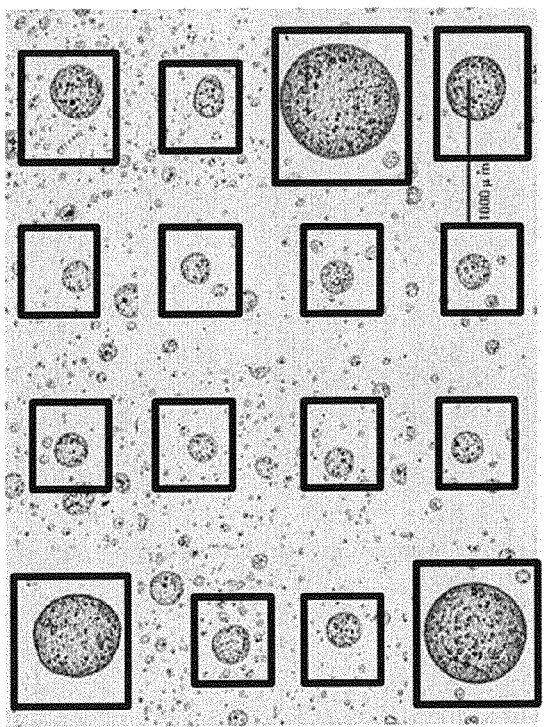
Figure 10:
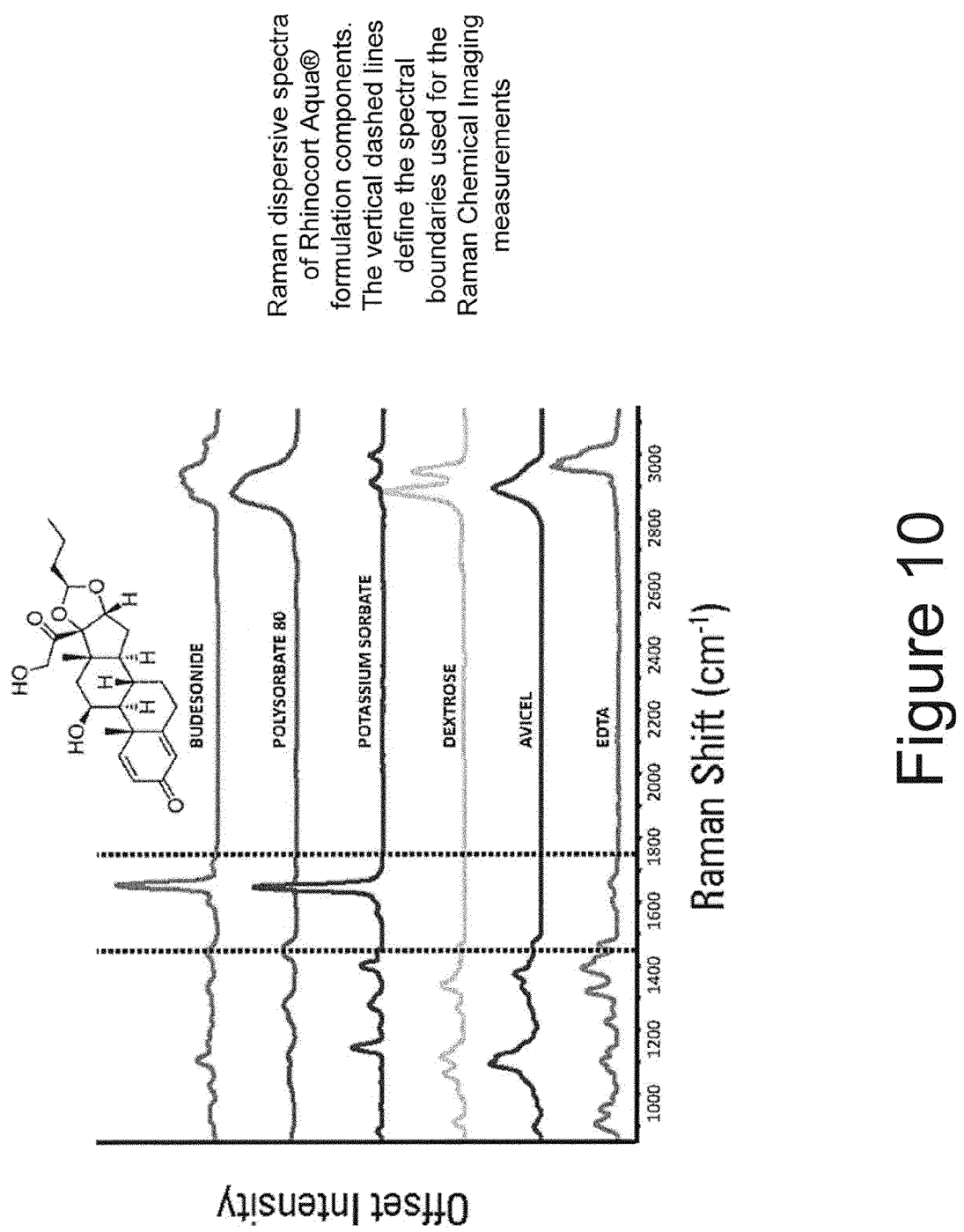
FIG. 10 represents Raman dispersive spectra of Rhinocort Aqua® formulation components.

Two different lots of a Rhinocort Aqua® nasal spray (32 mcg budesonide, AstraZeneca, Wilmington, Del.) with different expiration dates were acquired. Samples were prepared by shaking, priming (eight actuations each) and spraying in an upright position onto an inverted aluminum-coated glass microscope slide positioned approximately 15 cm above the spray nozzle. The microscope slides were then immediately turned upright and the nasal suspension droplets were allowed to dry. Actuated samples were analyzed to include actuation device influence as opposed to bulk samples. Sixteen (16) droplets varying in size and shape were randomly selected on the microscope slide for each batch (FIGS. 8 and 9). Optical microscopy and RCI were used to measure the budesonide PSD in each droplet, and the drug PSD data was assembled to yield a representative PSD for budesonide API for each batch. All data was collected using a FALCON II™ Wide-Field Raman Chemical Imaging System (ChemImage Corporation, Pittsburgh, Pa.) with 532 nm laser excitation (FIG. 4). Brightfield reflectance and Raman chemical images were collected over the necessary number of fields of view yielding a sampling area sufficient to image each individual droplet without significant oversampling. The spectral range for the RCI measurements was chosen to include a characteristic C=C feature at 1657 $cm^{-1}$, that can be used to discriminate budesonide from all other excipients in this particular formulation (FIG. 10). Imaging data was analyzed using ChemImage Xpert™ software package (Version 2.3.1, ChemImage Corporation, Pittsburgh, Pa.) yielding both the Raman/brightfield fusion images as well as the budesonide particle statistics.

Figure 11:
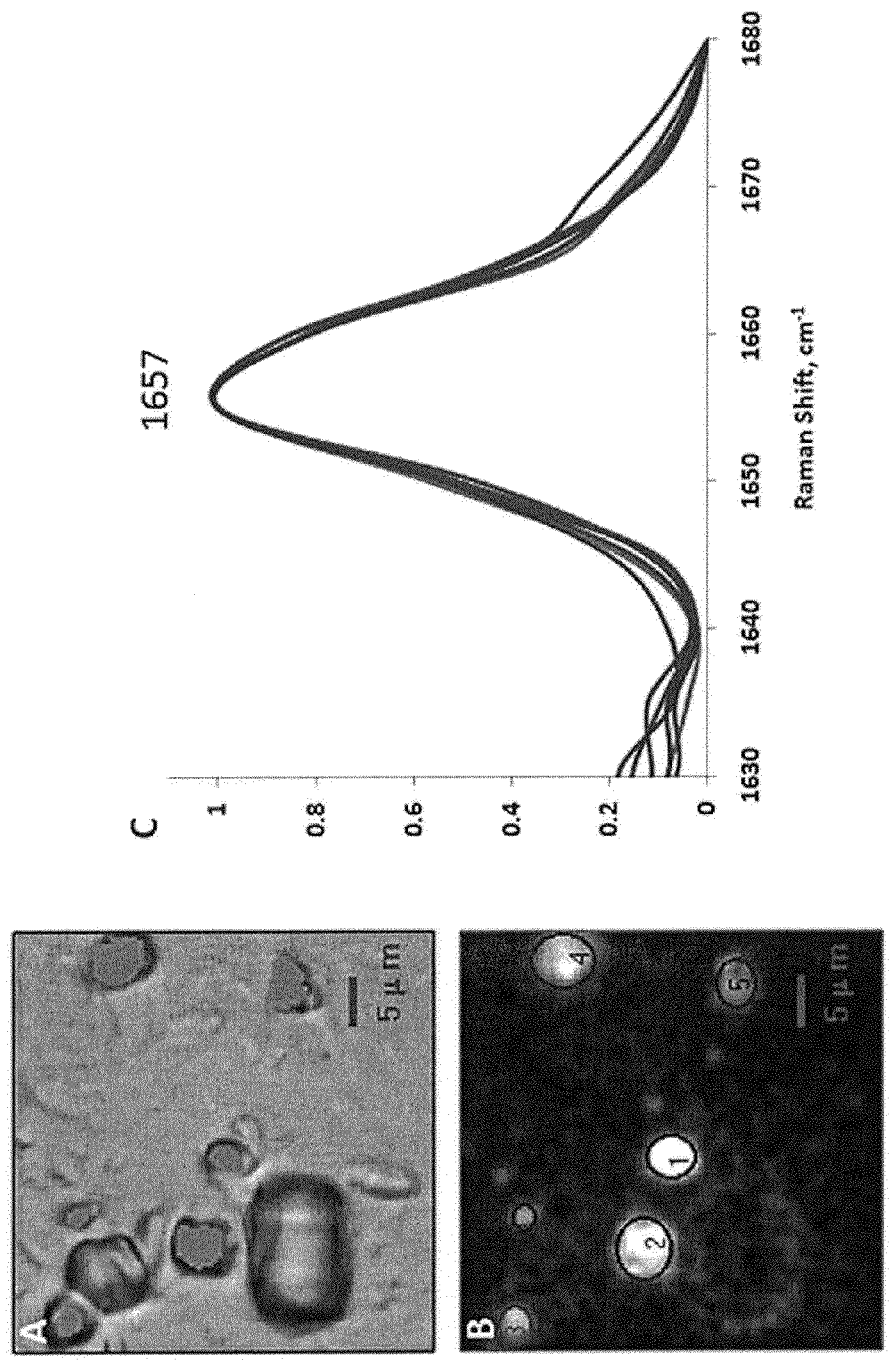
FIG. 11 illustrates a brightfield reflectance/processed Raman fusion image of a single field of view of budesonide particles in a Rhinocort Aqua® droplet and associated spectra.

Brightfield Raman chemical fusion images of representative field of view selected for ISPS analysis is shown in FIG. 11, along with corresponding spectra. Automated particle sizing was performed using the RCI hypercube. The intensity within the spectral peak was integrated at each pixel to create a working image with a higher signal-to-noise ratio than the peak intensity plane alone. This also served as a method of baseline correction. The resultant working image showed potential API particles as bright regions on a dark background (FIG. 5B). A particle detection threshold equal to three standard deviations of the noise above the average background intensity was applied to the working image to detect objects for size measurement and verification of the particle spectral signatures (FIG. 5C).

Sizing the objects of interest was performed by individually processing the edges and brightness of each object. Edges of each object were detected by computing the gradient of the working image to find the pixels where the intensity changes most rapidly. A small copy of each detected object was cropped from the working image, and pixels located at ht steepest edges of the objects within this cropped region were identified. The average intensity of the edge pixels was computed and used as a threshold within the cropped region. Neighboring objects which were originally grouped into large masses by the global threshold there were separated into individual objects. A unique threshold based on the intensity at object edges was iteratively determined for each object. Standard image analysis routines were then used to compute the sizes and shapes of detected objects. The spectral shape of each object was verified after detection and sizing. A "shape" constraint was imposed on the average spectrum of an object so that it must have a continuously rising leading edge, and a continuously falling trailing edge, i.e., it must look like a peak to a human observer. A brightness constraint determined whether or not a particle counted, meaning the particle had sufficient contrast to be recognizable above background noise. Rose's Criterion was used to make this determination wherein object intensity should be five standard deviations above the average background.

Figure 14:
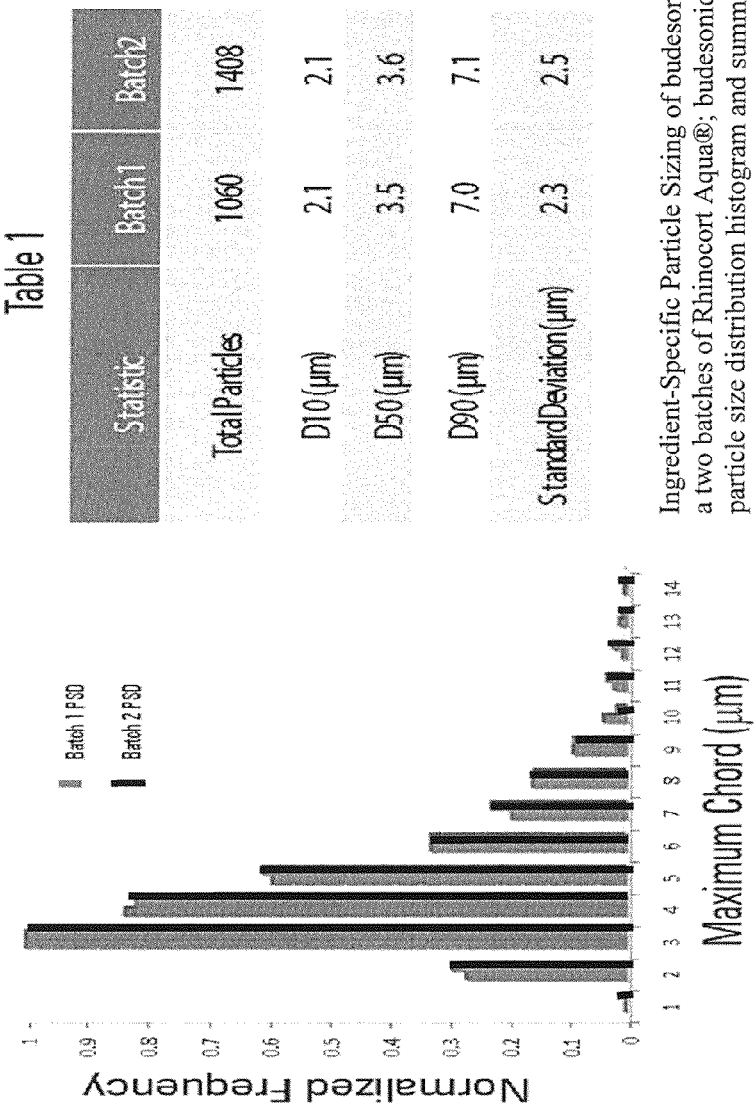
FIG. 14 represents a budesonide particle size distribution histogram and summary table of particle size distribution.

Brightfield/Raman chemical fusion images were obtained for all droplets analyzed (FIGS. 12 and 13). The PSD based on maximum chord, the longest distance across the particle, was statistically evaluated for D10, D50, D90 and standard deviation for each batch (FIG. 14). Table 1 shows a good agreement of the metric values for drug PSD between two batches. For a normal distribution, the Taylor approach may compare two populations based on a mean and standard deviation using a defined confidence interval. However, the achieved particle size distribution is not normal. A two-sample Kolmogrov-Smirnov goodness-of-fit hypothesis test was performed on this data set where the null hypothesis was accepted at the 95% confidence level meaning that the drug PSD populations are the same for these two batches.

ISPS based on wide-field RCI coupled with brightfield optical imaging demonstrated potential as a method for accurate particle size analysis and shape characterization. This approach can directly benefit batch release testing as well as the bioequivalence requirements for NDA and ANDA for corticosteroids in aqueous nasal spray suspension formulations. Automated data acquisition and image processing is shown to produce objective accurate drug particle sizes for comparison across multiple batches of a nasal spray suspension with sufficient representative sampling required for product quality assessment. High-fidelity, wide-field Raman chemical imaging with superior spectral and spatial resolution can also show advantages in identification of agglomerates and particle association.

What is claimed is:
1. A method comprising:
configuring a spectroscopic imaging device to: (a) irradiate a sample comprising at least one unknown particle to produce Raman scattered photons, and (b) collect the Raman scattered photons to generate a Raman chemical image representative of the sample;
integrating the intensity within the spectral peak at each pixel of the Raman chemical image to generate a working image; and
configuring a processor to:
(c) apply a first threshold to the working image wherein the first threshold is such that all particles in the sample are detected;
(d) select one of the detected particles;
(e) apply a second threshold to the working image to determine at least one geometric property of the selected particle, wherein the second threshold is unique to the selected particle such that the geometric property can be determined;
(f) analyze at least one spectrum, representative of the selected particle, wherein analyzing further comprises comparing at least one spectrum representative of the selected particle to at least one reference spectrum representative of a particle of interest; and
if comparing results in a match between the spectrum representative of the selected particle and the reference spectrum representative of the particle of interest, identifying the selected particle as a particle of interest; and
if comparing does not result in a match between the spectrum representative of the selected particle and the ref- erence spectrum representative of the particle of interest, identifying the selected particle as not a particle of interest.

2. The method of claim 1 further comprising repeating steps (d)-(f) for at least one other unknown particle present in the sample.

3. The method of claim 1 wherein the at least one geometric property comprises the size of the selected particle.

4. The method of claim 1 wherein the geometric property of the selected particle comprises at least one of: an area, a perimeter, a feret diameter, a maximum chord length, a shape factor, an aspect ratio, and combinations thereof.

5. The method of claim 1 wherein the geometric property of the selected particle comprises at least one of: particle size, morphology, spatial distribution, and combinations thereof.

6. The method of claim 1 further comprising fusing the working image with a brightfield image representative of the sample to generate a fused image representative of the sample.

7. The method of claim 6 further comprising analyzing the fused image to determine at least one geometric property of at least one unknown particle in the sample.

8. The method of claim 7 wherein the geometric property further comprises at least one of: particle size, morphology, spatial distribution, and combinations thereof.

9. The method of claim 7 wherein the geometric property further comprises at least one of: an area, a perimeter, a feret diameter, a maximum chord length, a shape factor, an aspect ratio, and combinations thereof.

10. The method of claim 1 wherein the second threshold comprises a fraction of the integrated peak intensity of the Raman spectrum corresponding to the selected particle.

11. The method of claim 10 wherein the fraction comprises one half.

12. The method of claim 1 wherein the second threshold comprises the integrated peak intensity of at least one Raman spectrum corresponding to at least one edge of the selected particle.

13. The method of claim 1 wherein the second threshold is determined by averaging the peak intensities of two or more Raman spectra corresponding to at least one edge or the selected particle.

14. The method of claim 1 wherein the second threshold is determining by a method comprising:
(a) applying a candidate second threshold to the working image;
assessing the effectiveness of the candidate second threshold; and
(i) if, based on the assessment, the candidate second threshold is effective, identifying the candidate second threshold as a second threshold unique to the selected particle, such that the geometric property can be determined, and
(ii) if based on the assessment, the candidate second threshold is not effective, repeating steps (a)-(b) for at least one other candidate second threshold.

15. The method of claim 14 wherein a candidate second threshold is determined to be effective when the integrated peak intensity of the selected particle is five standard deviations above the average background.

16. The method of claim 14 wherein the second threshold determination method is automated via software.

17. The method of claim 1 wherein comparing further comprises applying a chemometric technique to the working image.

18. The method of claim 17 wherein the chemometric technique further comprises at least one of: cluster analysis, principal component analysis (PCA), Cosine Correlation Analysis (CCA), Euclidian distance analysis (EDA), multivariate curve resolution (MCR), band target entropy method (BTEM), Mahalanobis distance (MD), adaptive subspace detector (ASO), multivariate curve resolution (MCR), and combinations thereof.

19. The method of claim 1 wherein the method is automated via software.

20. The method of claim 1 wherein the spectrum representative of the selected particle further comprises an average spectrum.

21. A method comprising:
configuring a spectroscopic imaging device to:
(a) irradiate a sample comprising at least one unknown particle of interest to thereby produce interacted photons wherein the interacted photons are selected from the group consisting of: Raman scattered by the sample, reflected by the sample, emitted by the sample, absorbed by the sample, and combinations thereof; and
configuring a processor to:
(b) collect the interacted photons to thereby generate a chemical image representative of the sample;
(c) apply a first threshold to the chemical image wherein the first threshold is such that all particles in the sample are detected;
(d) select one of the particles detected as a result of applying the first threshold;
(e) apply a second threshold to the chemical image to thereby determine at least one geometric property of the selected particle, wherein the second threshold is unique to the selected particle such that the geometric property can be determined; and
(f) analyze at least one spectrum representative of the selected particle, wherein analyzing further comprises comparing at least one spectrum representative of the selected particle to at least one reference spectrum representative of a particle of interest, and
if comparing results in a match between the spectrum representative of the selected particle and the reference spectrum representative of the particle of interest, identifying the selected particle as a particle of interest; and
if comparing does not result in a match between the spectrum representative of the selected particle and the reference spectrum representative of the particle of interest, identifying the selected particle as not a particle of interest.

22. The method of claim 21 wherein comparing further comprises applying a chemometric technique to the working image.

23. The method of claim 22 wherein the chemometric technique further comprises at least one of cluster analysis, principal component analysis (PCA), Cosine Correlation Analysis (CCA), Euclidian distance analysis (EDA), multivariate curve resolution (MCR), band target entropy method (BTEM), Mahalanobis distance (MD), adaptive subspace detector (ASD), multivariate curve resolution (MCR), and combinations thereof.

24. A method comprising:
configuring a spectroscopic imaging device to: (a) irradiate a sample comprising at least one unknown particle to produce Raman scattered photons, and (b) collect the Raman scattered photons to generate a Raman chemical image representative of the sample;
integrating the intensity within the spectral peak at each pixel of the Raman chemical image corresponding to at least two edges of the particle to generate a working image; and configuring a processor to:
(c) apply a first threshold to the working image wherein the first threshold is such that all particles in the sample are detected;
(d) select one of the detected particles;
(e) apply a second threshold to the working image, wherein the second threshold is unique to the selected particle such that the geometric property can be determined;
(f) analyze at least one spectrum representative of the selected particle, wherein analyzing further comprises comparing at least one spectrum representative of the selected particle to at least one reference spectrum representative of a particle of interest; and
if comparing results in a match between the spectrum representative of the selected particle and the reference spectrum representative of the particle of interest, identifying the selected particle as a particle of interest, and
if comparing does not result in a match between the spectrum representative of the selected particle and the reference spectrum representative of the particle of interest, identifying the selected particle as not a particle of interest.

25. The method of claim 24 wherein comparing further comprises applying a chemometric technique to the working image.

26. The method of claim 25 wherein the chemometric technique further comprises at least one of: cluster analysis, principal component analysis (PCA), Cosine Correlation Analysis (CCA), Euclidian distance analysis (EDA), multivariate curve resolution (MCR), band target entropy method (BTEM), Mahalanobis distance (MD), adaptive subspace detector (ASD), multivariate curve resolution (MCR), and combinations thereof.

* * * * *